United States Patent
Bialas

(10) Patent No.: US 9,439,023 B2
(45) Date of Patent: Sep. 6, 2016

(54) SYSTEM FOR DISPLAYING A MEDICAL DIAGNOSTIC RESULT

(76) Inventor: Tammo Bialas, Hamburg (DE)

( * ) Notice: Subject to any disclaimer, the term of this patent is extended or adjusted under 35 U.S.C. 154(b) by 463 days.

(21) Appl. No.: 13/808,812

(22) PCT Filed: Jul. 7, 2011

(86) PCT No.: PCT/EP2011/003371
§ 371 (c)(1),
(2), (4) Date: Aug. 29, 2013

(87) PCT Pub. No.: WO2012/003981
PCT Pub. Date: Jan. 12, 2012

(65) Prior Publication Data
US 2013/0337784 A1 Dec. 19, 2013

(30) Foreign Application Priority Data

Jul. 7, 2010 (DE) .................. 10 2010 026 478

(51) Int. Cl.
| | |
|---|---|
| *G06F 15/16* | (2006.01) |
| *H04W 4/00* | (2009.01) |
| *A61B 5/00* | (2006.01) |
| *G06F 19/00* | (2011.01) |
| *A61B 1/227* | (2006.01) |

(Continued)

(52) U.S. Cl.
CPC .............. *H04W 4/00* (2013.01); *A61B 5/0002* (2013.01); *G06F 19/3418* (2013.01); *G06F 19/3425* (2013.01); *A61B 1/227* (2013.01); *A61B 3/12* (2013.01); *A61B 5/0006* (2013.01); *A61B 5/021* (2013.01); *A61B 5/091* (2013.01); *A61B 5/145* (2013.01); *A61B 8/06* (2013.01); *A61B 2050/105* (2016.02); *A61B 2050/185* (2016.02); *B62B 1/26* (2013.01)

(58) Field of Classification Search
CPC ........ H04W 4/00; G06F 19/00; G06F 19/30; G06F 19/32; G06F 19/34; G06F 19/36; G06F 19/3425

See application file for complete search history.

(56) References Cited

U.S. PATENT DOCUMENTS

| | | | | |
|---|---|---|---|---|
| 4,062,604 A | * | 12/1977 | Popper | .......................... 312/211 |
| 4,491,375 A | * | 1/1985 | Ugalde | ...................... 312/249.9 |

(Continued)

FOREIGN PATENT DOCUMENTS

WO   WO 2008/083313   7/2008

OTHER PUBLICATIONS

Anonymous: "Telehealth & Telemedicine Communications Solution", Jun. 10, 2010, pp. 1-5 http://web.archive.org/web/20100610223158//www.ipix-communications.com/medical-and-telemedicine.html.*

(Continued)

*Primary Examiner* — Douglas Blair
(74) *Attorney, Agent, or Firm* — White & Case LLP

(57) ABSTRACT

The invention relates to a system for displaying a medical diagnostic result, comprising at least one diagnostic device having a data output outputting electronic data which represent a diagnostic result that has been obtained using the diagnostic device, and further comprising an electronic data line connection which directs the electronic data to a display device and that has a data line radio link having a radio transmitter and a radio receiver of a mobile radio network, the display device being designed to display the diagnostic result without delay, and the at least one diagnostic device and the radio transmitter being accommodated in a transport device.

8 Claims, 3 Drawing Sheets

(51) Int. Cl.
  *A61B 3/12* (2006.01)
  *A61B 5/021* (2006.01)
  *A61B 5/091* (2006.01)
  *A61B 5/145* (2006.01)
  *A61B 8/06* (2006.01)
  *B62B 1/26* (2006.01)

(56) References Cited

U.S. PATENT DOCUMENTS

| | | | |
|---|---|---|---|
| 4,724,844 A * | 2/1988 | Rafelson | 600/483 |
| 5,961,192 A * | 10/1999 | Bernart et al. | 312/223.3 |
| 6,176,559 B1 * | 1/2001 | Tiramani et al. | 312/108 |
| 2003/0080655 A1 * | 5/2003 | Goldberg | 312/290 |
| 2003/0139664 A1 * | 7/2003 | Hunt et al. | 600/407 |
| 2004/0186357 A1 | 9/2004 | Soderberg et al. | |
| 2005/0122015 A1 * | 6/2005 | Hightower | 312/334.5 |
| 2007/0228680 A1 | 10/2007 | Reppert et al. | |
| 2008/0116093 A1 | 5/2008 | Felten et al. | |
| 2008/0281301 A1 * | 11/2008 | DeBoer et al. | 606/1 |
| 2010/0052293 A1 | 3/2010 | Brooks et al. | |
| 2010/0277046 A1 * | 11/2010 | Kuo | 312/264 |
| 2010/0324380 A1 * | 12/2010 | Perkins et al. | 600/301 |
| 2012/0253509 A1 * | 10/2012 | Garda et al. | 700/235 |
| 2012/0290259 A1 * | 11/2012 | McAfee et al. | 702/155 |
| 2013/0265844 A1 * | 10/2013 | Yuan | B01F 15/00753 366/110 |

OTHER PUBLICATIONS

Anonymous: "Telehealth & Telemedicine Communications Solutions", Jun. 10, 2010, XP002664424, retrieved from the Internet: URL:http://web.archive.org/web/20100610223158//www.ipx-communications.com/medical-and-telemedicine.html [retrieved on Nov. 25, 2011].

Written Opinion of the International Searching Authority issued in International Application No. PCT/EP2011/003371 on Jan. 17, 2013.

* cited by examiner

SYSTEM FOR DISPLAYING A MEDICAL DIAGNOSTIC RESULT

The present invention relates to a system for displaying a medical diagnostic result and to a method for applying the system.

For diagnostic purposes, a medical practitioner and patient are usually together in the treatment room of a surgery, a hospital or, for example, in the case of emergencies at the patient's home or in an emergency ambulance. The medical practitioner examines the patient, with the aid of diagnostic instruments as well, and observes the diagnostic result—to the extent that it is even available immediately—on a corresponding display device of the respective diagnostic instrument.

The possibilities for diagnosis are severely restricted in the case of home visits and for treatment in emergencies in particular (i.e. if the patient does not come to the medical practitioner but the medical practitioner comes to the patient): since most diagnostic instruments have a certain weight and volume meaning that they cannot readily be carried about in a "physician's bag", many diagnoses are not performed in such a situation or require the assistance of an appropriately equipped emergency ambulance or ambulance.

Compared to diagnostics in the hospital or in the rooms of a surgery, a further problem in such a situation lies in the diagnosing medical practitioner not having the option of consulting a colleague, for example if he is unsure about the diagnosis and wishes to obtain a second opinion. In the hospital or in the surgery, he can ask his colleague to come by in person and look at the diagnosis on the display. He does not have this option in the case of home visits or emergencies outside.

The object of the present invention is to develop a system for displaying a medical diagnostic result, which improves the diagnostic possibilities, particularly outside of equipped medical treatment rooms.

This object is achieved by a system having the features of claim 1. Preferred embodiments are specified in the dependent claims.

According to the invention, a system for displaying a medical diagnostic result has at least one diagnostic instrument and an electronic data line connection, which feeds a diagnostic result in the form of electronic data to a display device from the data output of the diagnostic instrument. According to the invention, the data line connection has a cellular link. In other words, the electronic data which represents the diagnostic result is transmitted for at least some of the distance by radio by means of a radio transmitter and a radio receiver of a cellular network on its path from the data output of the diagnostic instrument to the display device.

This cellular link advantageously renders it possible to use the diagnostic instrument on the move and to consult a medical practitioner situated somewhere else when evaluating the diagnostic result. The distance thereto is bridged for the electronic data representing the diagnostic result by means of the cellular link. The display device at the other location is therefore configured and able to display the diagnostic result without time delay. When using the device according to the invention, the diagnostic result can readily also be buffer stored and then still shown with time-lag at a later stage. Within the meaning of the invention, without time delay only means that the diagnostic result is, at best, only buffer stored briefly for such a length of time (for example in order to undertake storage processes in the display device required for the display) that the buffer storage occurs without additional advantage compared to display in actual fact completely without time delay or, in other words, that there can be a discussion in respect of the diagnostic result between a medical practitioner at the display device and a person with the patient as if without time delay after making the diagnosis.

In a particularly simple, technically systematic way, the radio transmitter according to the invention can be implemented in a PC, in particular in a mobile PC such as e.g. a notebook or a tablet computer. It is well known that various technical cellular transmitters are available for these (conventionally for mobile Internet access in particular), such as e.g. a UMTS data card (for example with a USB plug or as PCMCIA card) in order to mention but examples of various technical possibilities.

This inclusion of a PC in the system according to the invention furthermore has the advantage of connecting a plurality of diagnostic instruments in the system with the PC to form a local network (e.g. a LAN and/or WLAN) and/or of simply connecting these diagnostic instruments to the PC (by means of cables, but also, for example, wirelessly, e.g. Bluetooth and/or infrared). The PC can then already have software with the aid of which diagnostic results of the various diagnostic instruments are combined, e.g. in tabular form, or preprocessed in any other way before they are transmitted on to the display device by means of the cellular link.

In order to enable the mobility of the at least one diagnostic instrument and preferably of the plurality of diagnostic instruments of the PC in an ergonomic fashion, the at least one diagnostic instrument, the radio transmitter and optionally the PC are arranged in a transport device, preferably a transport container, particularly preferably a rolling case. The rolling case can preferably (for example in the style of a "board case") be equipped with, for example, two rollers and a (possibly extendable) pulling handle. However, the transport container is preferably larger than a "board case" in order preferably to house a plurality of diagnostic instruments.

The transport container preferably has shell elements, which are connected to one another in pivotable fashion by means of joints for opening and closing purposes. By way of example, the shell elements can have an external shell made of aluminum or polycarbonate, as has proven its worth for light and robust travel suitcases. It is preferable for at least two shell elements (cover and actual container), but also for a plurality of pivotably connected shell elements, for example in the style of a trunk, to be feasible according to the invention, in order also to be able to house as ergonomically as possible a plurality of diagnostic instruments in them such that they are arranged in operable fashion in the opened transport container. When opened (with opened-up shell elements), the transport container is preferably inherently stable and self-supported. This means that it does not (readily) fall over when opened, for example when a treating medical practitioner is operating the diagnostic instruments situated therein.

In order to enable a diagnosis which is as comprehensive as possible, the transport container for example houses the following medical diagnostic instruments and aids:

Cardiac reader: a dry-chemical rapid tester for measuring proteins circulating in the blood for molecular diagnosis and differential diagnosis of cardiovascular diseases, Dermatoscope: an optical magnification light mirror for identifying skin diseases, EEG: an electronic recording instrument for brain wave curves for diagnosing neurological and psychiatric diseases, EKG and long-term EKG: an electronic recording instrument for cardiac current curves for cardiological diagnosis of heart diseases, Funduscope (retinoscope/ophthalmoscope): an electronic ophthalmoscope for ophthalmological findings of the eye fundus including the retina, Glucose multi-test instrument: a dry-chemical rapid tester for measuring blood sugar, blood fats, cholesterol and lactic acid (lactate), Long-term sphygmomanometer: an automatic, time-controlled sphygmomanometer for measuring and recording the blood pressure over a number of hours, Otoscope: an electronic otoscope for otological findings of the outer ear, the auditory canal and the eardrum (middle ear), Pulse oximeter: an electronic measuring instrument for oxygen saturation in the capillary blood by means of a transcutaneous measurement using a finger clip, Quick rapid tester: a dry-chemical rapid tester for measuring the Quick's value as an indicator of natural blood clotting and for monitoring medicinal anticoagulation therapy (anticoagulation), Spirometer: a pneumatic rapid tester for measuring the respiratory flow volume and calculating the airway resistance for diagnosing the lung function, Pocket Doppler: a high-frequency ultrasound scanner with Doppler function for diagnosing the flow speed and flow properties of arterial and venous blood in the vessels, Ultrasound scanner (sonographic scanner): a high-frequency ultrasound scanner for anatomical overview and diagnosis of the epigastric region (abdominal region), the chest and the heart (cardial), the thyroid gland and the blood vessels leading to the brain (cranial), Urine rapid tester: a dry-chemical rapid tester for analyzing and semi-quantitatively measuring the urine state, and also, for example, the following non-medical instruments and aids:

DigiCam: a digital camera for conciliar video conferences, a health-card reader an electronic cash card reader, the notebook.

The above-described and further features and advantages of the system according to the invention are illustrated below in exemplary fashion with reference to the attached drawings.

Figure 1:
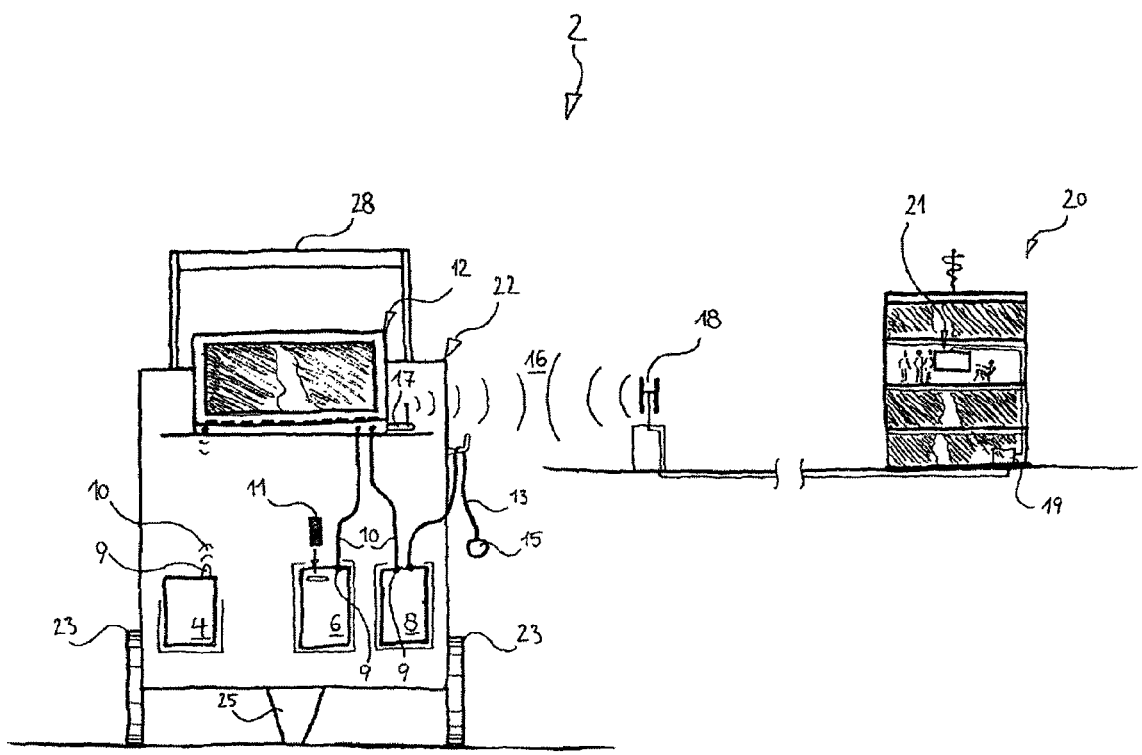
FIG. 1 is a schematic overview of a system according to the invention.

FIG. 1 schematically shows a system 2 for displaying a medical diagnostic result (not illustrated). The system 2 has three diagnostic instruments 4, 6 and 8, respectively with a data output 9, which outputs electronic data (not illustrated) respectively representing a diagnostic result (not illustrated) as part of the overall diagnostic result established by the respective diagnostic instrument 4, 6 and 8.

The diagnostic instrument 4 is a hand-held instrument, which the diagnosing medical practitioner (not illustrated) can pick up for use and which has a wireless data line connection 10 to the PC 12 by means of a Bluetooth interface as data output 9.

The diagnostic instrument 6 is a stand-alone unit, into which the diagnosing medical practitioner (not illustrated) can insert a test strip 11 and which has a wired data line connection 10 to the PC 12 by means of a plug as data output 9.

The diagnostic instrument 8 is a stand-alone unit, of which the diagnosing medical practitioner (not illustrated) can pick up a diagnosis head 15, attached by cable 13, and which has a wired data line connection 10 to the PC 12 by means of a plug as data output 9.

The data outputs 9 have a data line connection 10 to the PC 12. This notebook 12, as part of a cellular link 16, has a cellular transmitter 17 in the form of a PCMCIA-UMTS data card 17, which transmits the electronic data to a cellular receiver 18 of a cellular network (not illustrated). From there, the electronic data is sent to a server 19 in a medical center of excellence 20. The server 19 immediately (i.e. in real-time) provides for the electronic data, which represents the overall result of the diagnosis, to be displayed on a display device 21, such that, for example, medical specialists see it there, discuss it and can also send back their feedback to the diagnosing medical practitioner who is with the patient (e.g. by telephone, also as video conference, or by email). To this end, the system can also have a voice and/or text communication link between communication input/output equipment in the transport container and communication input/output equipment in the display device which then, according to the invention, likewise has a radio link.

Figure 2:
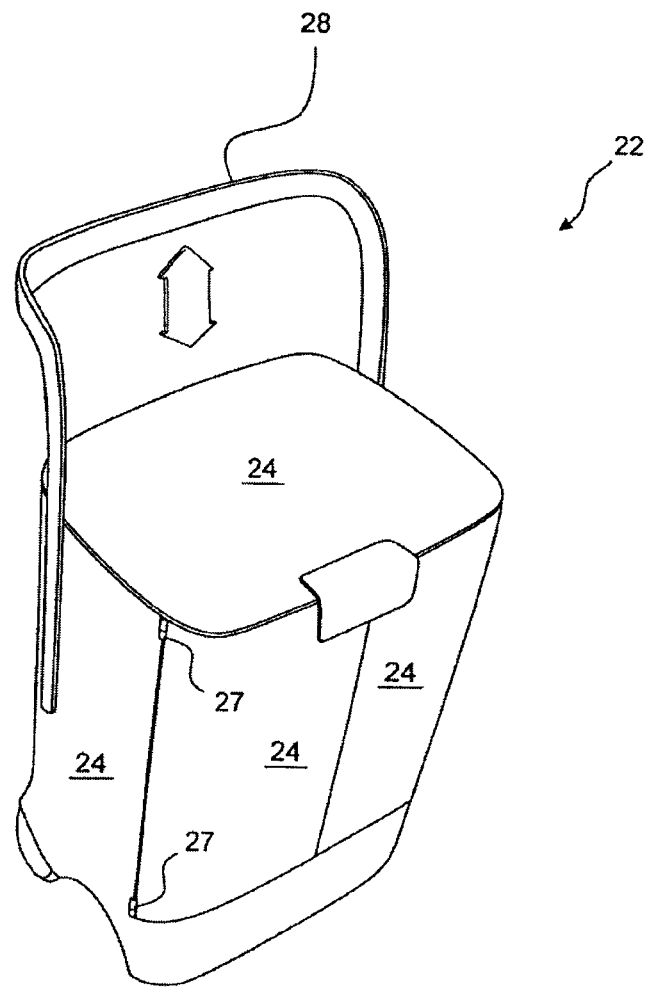
FIG. 2 is a spatial view of a closed rolling case according to the invention and FIG. 3 is a spatial view of the rolling case from FIG. 2 when opened.
Figure 3:
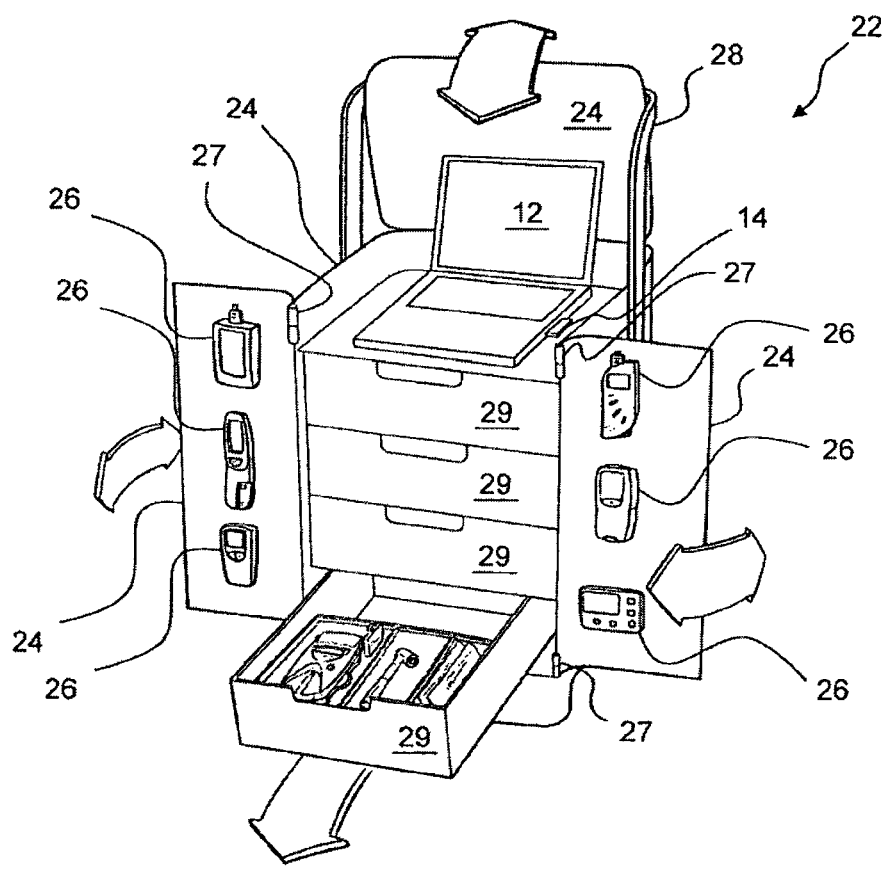

FIG. 2 shows a spatial view of a closed rolling case 22 and FIG. 3 shows a spatial view of the opened rolling case 22, which is also illustrated schematically in FIG. 1. This transport container 22 has two rollers 23 and, in front of these, a pedestal 25, a plurality of shell elements 24, which are connected to one another in pivotable fashion by means of joints 27 for opening and closing purposes, an extendable handle 28 and drawers 29.

In one of the opened-up shell elements 24, which forms a type of "lectern" on the thus opened transport container 22 which stands in inherently stable fashion on the rollers 22 and the pedestal 25, an opened-up notebook 12 is affixed in operable fashion. The PC 12 has a UMTS data card as cellular transmitter. Diagnostic instruments 26 are likewise affixed in the shell elements 24 such that they can be operated by a user—depending on the type and function of the respective instrument 26 even without having to be taken out of the transport container 22.

The rolling case 22 together with its contents as per FIG. 2 and FIG. 3 can serve as mobile diagnosis center in the system 2 as per FIG. 1. It also enables the emergency medical practitioner to provide diagnostic results without time delay, i.e. in real-time, to colleagues via the cellular link in order, for example, to discuss the result by cellular telephone or another communication link and immediately take appropriate action on the patient. According to the invention, this colleague support can be promoted further by virtue of the fact that video data is additionally also transmitted via the cellular link, which data the treating medical practitioner has recorded at the patient by means of e.g. a CCD camera, which is then one of the diagnostic instruments (not illustrated).

However, these improvements can benefit not only emergency medicine, but also enable improvements of home-visit medical care by virtue of the fact that the traveling medical practitioner needs not necessarily be competent to the last detail in medical specialisms. Since, for example, if he identifies that an orthopedic problem of the patient exceeds his specialist knowledge in internal medicine, it is enough for him to recognize orthopedics as the relevant field in order to consult an orthopedic surgeon in a targeted fashion by means of the system according to the invention using the cellular link and also, if necessary, to take suitable measures immediately on the patient under the instructions of the orthopedic surgeon. He is generally qualified to do this using his general medical capabilities, even as a specialist for internal medicine.

The system according to the invention thus also renders it possible to let a general medical practitioner without specific specialist qualification (or even a correspondingly well educated "home visit specialist"—e.g. a nurse or a medical assistant with additional schooling appropriate to the diagnostic system) carry out the home visits. The inclusion of the system according to the invention in a suitable organization of home visitors and a team of specialists in a medical center of excellence (for example as per FIG. 1, reference sign 20 renders it possible, according to the invention, to lift home-visit medical care to a level which up until now has only been achieved by outpatient or even inpatient care.

The invention claimed is:

1. A system for displaying a medical diagnostic result, the system comprising at least three diagnostic instruments of at least three different modalities, each diagnostic instrument having a data output which outputs electronic data representing a diagnostic result established by the diagnostic instrument, wherein at least one instrument is a non-imaging instrument;

the system comprising a radio transmitter in communication over a data line radio link with a radio receiver of a cellular network, the system communicating electronic data comprising diagnostic results to a server and a remote display device via an electronic data line connection over the radio line radio link without time delay; and the system optionally further comprising a computer;

the system further comprising a portable and transportable self-supporting transport container;

wherein the diagnostic instruments and the radio transmitter and optionally the computer are arranged in the portable and transportable self-supporting transport container in the form of a rolling case having a handle; a top cover which opens to form a lectern on the transport container; one or more front doors which can be opened and closed and which enclose a plurality of interior drawers which open in a slideable manner; and fasteners on an interior surface of the one or more front doors for affixing diagnostic equipment;

the front of the top cover closes flush with the top of the front door, and the front doors and the top cover enclose the drawers and the platform where the computer rests; and the diagnostic instruments and/or the computer are arranged in operable fashion in the opened transport container.

2. The system according to claim 1, wherein the computer is a PC, a notebook, or a tablet computer, and the radio transmitter is a cellular transmitter located in the computer.

3. The system according to claim 1, wherein the transport container has shell elements which are connected to one another in pivotable fashion by means of joints for opening and closing purposes.

4. The system according to claim 3, wherein the diagnostic instruments, the radio transmitter, and/or the computer are arranged in two or more of the shell elements.

5. The system according to claim 4, wherein the transport container, when opened, stands in an inherently stable fashion on a substantially horizontal, planar floor.

6. The system according to claim 1, wherein the cellular transmitter is a UMTS data card.

7. The system according to claim 1, wherein the different modalities are selected from the group consisting of ultrasound imaging, electrical signals, light signals, air flows, blood flows, and dry lab tests.

8. The system according to claim 1, wherein the transport container comprises a self-supporting rolling case having an extendable handle and a pivotably-connected top cover.

\* \* \* \* \*